(12) United States Patent
Lee et al.

(10) Patent No.: US 12,385,020 B1
(45) Date of Patent: Aug. 12, 2025

(54) 5-DEHYDRO-2-DEOXYGLUCONOKINASE VARIANT AND METHOD FOR PRODUCING 5'-INOSINIC ACID USING SAME

(71) Applicant: DAESANG CORPORATION, Seoul (KR)

(72) Inventors: Sun Hee Lee, Seoul (KR); Tae Yeol Choi, Seoul (KR); Hyun Ho Kim, Seoul (KR); Dong Hyun Kim, Seoul (KR); Hyun Sook Kim, Seoul (KR); Jong Hwan Shin, Seoul (KR)

(73) Assignee: DAESANG CORPORATION, Seoul (KR)

( * ) Notice: Subject to any disclaimer, the term of this patent is extended or adjusted under 35 U.S.C. 154(b) by 0 days.

(21) Appl. No.: 18/879,995

(22) PCT Filed: Aug. 31, 2023

(86) PCT No.: PCT/KR2023/012969
§ 371 (c)(1),
(2) Date: Dec. 30, 2024

(87) PCT Pub. No.: WO2024/210281
PCT Pub. Date: Oct. 10, 2024

(30) Foreign Application Priority Data

Apr. 6, 2023 (KR) .................. 10-2023-0045161

(51) Int. Cl.
*C12N 9/12* (2006.01)
*C12P 19/32* (2006.01)

(52) U.S. Cl.
CPC ............ *C12N 9/1205* (2013.01); *C12P 19/32* (2013.01); *C12Y 207/01092* (2013.01)

(58) Field of Classification Search
CPC .................................................. C12N 9/1205
See application file for complete search history.

(56) References Cited

FOREIGN PATENT DOCUMENTS

| KR | 10-1166027 | 7/2012 |
|----|------------|--------|
| KR | 10-2016-0078694 | 7/2016 |
| KR | 10-1904675 | 10/2018 |
| KR | 10-1916611 | 11/2018 |
| KR | 10-1916622 | 11/2018 |

OTHER PUBLICATIONS

International Search Report issued Jan. 19, 2024 in International (PCT) Application No. PCT/KR2023/012969.
Zuniga-Soto, Evelyn et al., "Insights into the transcriptomic response of the plant engineering bacterium *Ensifer adhaerens* OV14 during transformation", Scientific Reports, 2019, vol. 9, No. 10344, pp. 1-17.

*Primary Examiner* — Suzanne M Noakes
(74) *Attorney, Agent, or Firm* — Wenderoth, Lind & Ponack, L.L.P.

(57) ABSTRACT

The present invention relates to a novel 5-dehydro-2-deoxygluconokinase variant and a method of producing 5'-inosinic acid using the same. The 5-dehydro-2-deoxygluconokinase variant is obtained by substituting one or more amino acids in the amino acid sequence constituting 5-dehydro-2-deoxygluconokinase to change the activity of the protein, and a recombinant microorganism comprising the 5-dehydro-2-deoxygluconokinase variant is capable of efficiently producing 5'-inosinic acid.

7 Claims, 1 Drawing Sheet
Specification includes a Sequence Listing.

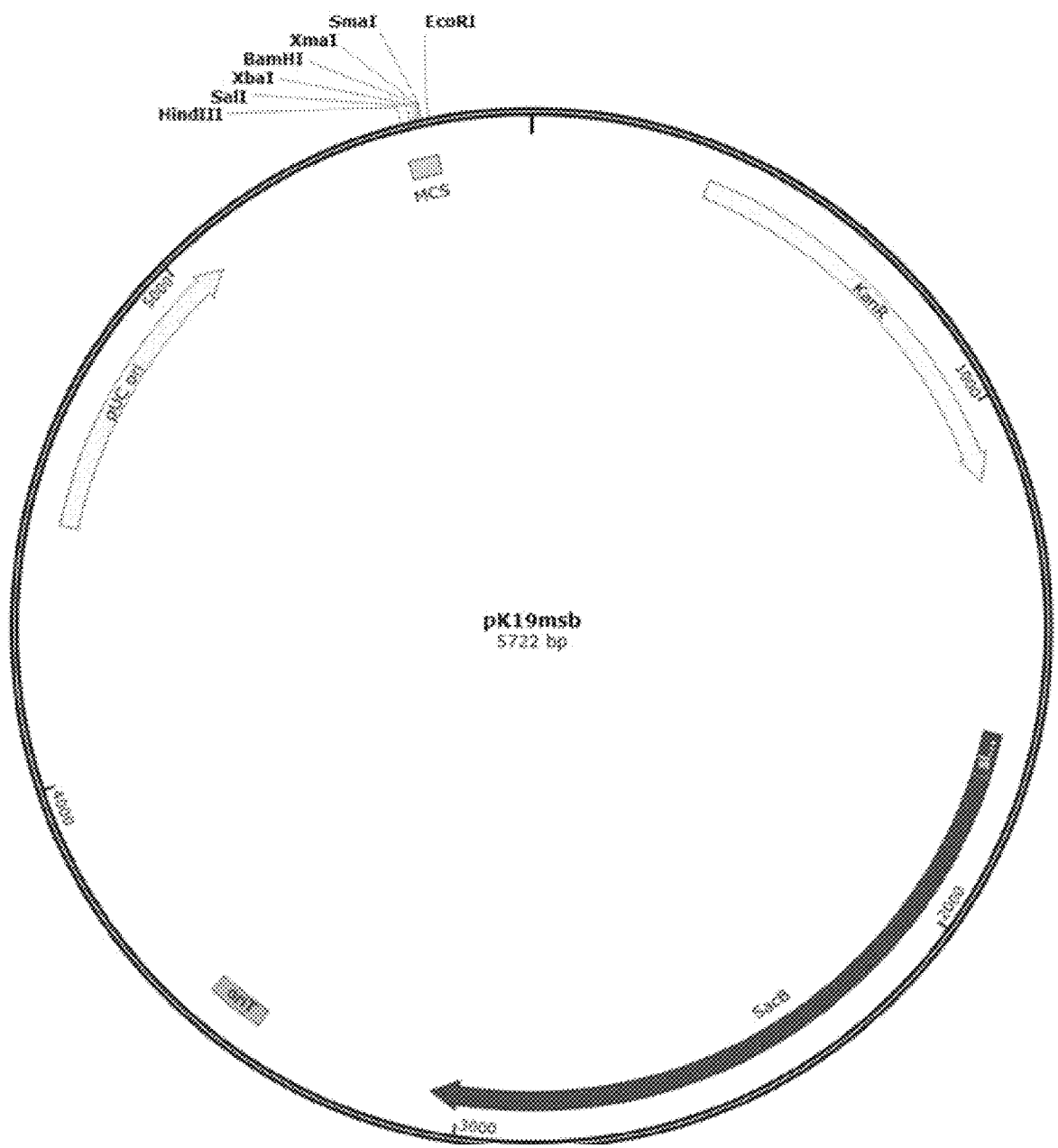

5-DEHYDRO-2-DEOXYGLUCONOKINASE VARIANT AND METHOD FOR PRODUCING 5'-INOSINIC ACID USING SAME

SEQUENCE LISTING

A sequence listing in electronic (XML file) format is filed with this application and incorporated herein by reference. The name of the XML file is "Sequence_Listing-1948A.xml"; the file was created on Dec. 29, 2024: the size of the file is 17.022 bytes.

TECHNICAL FIELD

The present invention relates to a novel 5-dehydro-2-deoxygluconokinase variant and a method of producing 5'-inosinic acid using the same.

BACKGROUND ART

5'-inosinic acid (or inosine monophosphate (IMP)) is an intermediate in the metabolic system of nucleic acid biosynthesis, and not only plays an important physiological role in the bodies of plants and animals, but is also used in various applications, including food, medicine, and various medical applications. In particular, 5'-inosinic acid is a nucleic acid-based seasoning, which has drawn much attention as a savory seasoning, because it has significant synergistic effects on taste when used together with monosodium glutamate (MSG)

Methods for producing 5'-inosinic acid include a method of enzymatically degrading ribonucleic acid extracted from yeast cells, a method of chemically phosphorylating inosine produced by fermentation, etc. Recently, a method of culturing a 5'-inosinic acid-producing microorganism and recovering 5'-inosinic acid accumulated in the medium has been mainly used.

For the production of 5'-inosinic acid using microorganisms, in order to improve the efficiency of production of 5'-inosinic acid, there has been development of a variety of recombinant strains or mutant strains having excellent 5'-inosinic acid productivity by applying genetic recombination technology to microorganisms such as *Escherichia coli* and *Corynebacterium*, which are widely used in the production of useful substances such as nucleic acids or L-amino acids, and methods of producing 5'-inosinic acid using the same. In particular, there have been attempts to increase the production of 5'-inosinic acid by targeting genes such as enzymes, transcription factors and transport proteins, which are involved in the biosynthetic pathway of 5'-inosinic acid, or by inducing mutations in promoters that regulate the expression of these genes. However, there are dozens to hundreds of types of proteins such as enzymes, transcription factors and transport proteins, which are involved directly or indirectly in the production of 5'-inosinic acid, and thus much research is still needed on the increase in 5'-inosinic acid productivity by changes in the activity of these proteins.

PRIOR ART DOCUMENTS

Patent Documents

Korean Patent No. 10-116602

DISCLOSURE

Technical Problem

An object of present invention is to provide a novel 5-dehydro-2-deoxygluconokinase variant.

Another object of the present invention is to provide a polynucleotide encoding the variant.

Still another object of the present invention is to provide a transformant comprising the variant or polynucleotide.

Yet another object of the present invention is to provide a method of producing 5'-inosinic acid using the transformant.

Technical Solution

One aspect of the present invention provides a 5-dehydro-2-deoxygluconokinase variant consisting of the amino acid sequence of SEQ ID NO: 2 in which serine at position 146 in the amino acid sequence of SEQ ID NO: 4 is substituted with asparagine.

As used in the present invention, the term "5-dehydro-2-deoxygluconokinase catalyzes a reaction that produces ADP and 6-phospho-5-dehydro-2-deoxy-D-gluconate using ATP and 5-dehydro-2-deoxy-D-gluconate as substrates, and it may be a polypeptide or protein consisting of the amino acid sequence of SEQ ID NO: 4 and having 5-dehydro-2-deoxygluconokinase activity.

Information on the nucleic acid and protein sequences of the 5-dehydro-2-deoxygluconokinase is available from known sequence databases (e.g., GenBank, UniProt).

According to one embodiment of the present invention, the 5-dehydro-2-deoxygluconokinase may be encoded by the nucleotide sequence of SEQ ID NO: 3.

The amino acid sequence of the 5-dehydro-2-deoxygluconokinase according to the present invention or the nucleotide sequence encoding the same may include a nucleotide sequence or amino acid sequence having at least 70%, 75%, 80%, 85%, 90%, 95%, 96%, 97%, 98%, 99 or 100% homology or identity to the amino acid sequence of SEQ ID NO: 4 or the nucleotide sequence of SEQ ID NO: 3. As used herein, the term "homology" or "identity" means the percentage rate of identity between two sequences, which is determined by aligning the reference nucleotide sequence or amino acid sequence and any other nucleotide sequence or amino acid sequence to correspond to each other as much as possible and analyzing the aligned sequences.

According to one embodiment of the present invention, the 5-dehydro-2-deoxygluconokinase may be derived from wild-type *Corynebacterium stationis*.

As used in the present invention, the term "variant" refers to a protein that has an amino acid sequence different from the amino acid sequence before mutation by the conservative substitution and/or modification of one or more amino acids at the N-terminus, C-terminus of and/or within the amino acid sequence, which result(s) from mutation in the nucleotide sequence of the gene encoding the protein, but retains the functions or properties of the protein before mutation. As used herein, the term "conservative substitution" means substituting one amino acid with another amino acid having similar structural and/or chemical properties. The conservative substitution may have little or no impact on the activity of the protein or polypeptide. In addition, the term "modification" refers to substitution, insertion, deletion, or the like of one or more amino acids. The amino acid is selected from among alanine (Ala, A), isoleucine (Ile, I), valine (Val, V), leucine (Leu, L), methionine (Met, M), asparagine (Asn, N), cysteine (Cys, C), glutamine (Gln, Q), serine (Ser, S), threonine (Thr, T), phenylalanine (Phe, F), tryptophan (Trp, W), tyrosine (Tyr, Y), aspartic acid (Asp, D), glutamic acid (Glu, E), arginine (Arg, R), histidine (His, H), lysine (Lys, K), glycine (Gly, G), and proline (Pro, P).

In addition, some variants include those in which one or more portions, such as an N-terminal leader sequence or transmembrane domain, have been removed, or those in which a portion has been removed from the N- and/or C-terminus of a mature protein.

The variant may have increased (enhanced), unchanged, or decreased (weakened) ability compared to that of the protein before mutation. Here, the term "increased or enhanced" includes: a case in which the activity of the protein itself has increased compared to the activity of the protein before mutation; a case in which the overall activity of the protein in the cell is higher than that in the wild-type strain or the strain expressing the protein before mutation due to increased expression or translation of the gene encoding the protein; and a combination thereof. In addition, the term "decreased or weakened" includes: a case in which the activity of the protein itself has decreased compared to the activity of the protein before mutation; a case in which the overall activity of the protein in the cell is lower than that in the wild-type strain or the strain expressing the protein before mutation due to reduced expression or translation of the gene encoding the protein; and a combination thereof. In the present invention, the term "variant" may be used interchangeably with terms such as variant type, modification, variant polypeptide, mutated protein, mutation, and the like.

The 5-dehydro-2-deoxygluconokinase variant according to the present invention may comprise an amino acid sequence having at least 70%, 75%, 80%, 85%, 90%, 95%, 96%, 97%, 98s, 99% or 100% homology or identity to the amino acid sequence of SEQ ID NO: 2.

Another aspect of the present invention provides a polynucleotide encoding the 5-dehydro-2-deoxygluconokinase variant.

As used in the present invention, the term "polynucleotide" refers to a DNA or RNA strand having a certain length or more, which is a long-chain polymer of nucleotides formed by linking nucleotide monomers via covalent bonds. More specifically, the term "polynucleotide" refers to a polynucleotide fragment encoding the variant.

According to one embodiment, the polynucleotide may comprise a nucleotide sequence encoding the amino acid sequence of SEQ ID NO: 2.

More specifically, the polynucleotide may comprise the nucleotide sequence of SEQ ID NO: 1 in which nucleotide "g" at position 437 in the nucleotide sequence of SEQ ID NO: 3 encoding 5-dehydro-2-deoxygluconokinase is substituted with nucleotide "a".

Still another aspect of the present invention provides a vector comprising a polynucleotide encoding the 5-dehydro-2-deoxygluconokinase variant.

Yet another aspect of the present invention provides a transformant comprising the 5-dehydro-2-deoxygluconokinase variant or the polynucleotide.

As used in the present invention, the term "vector" refers to any type of nucleic acid sequence transfer structure that is used as a means for transferring and expressing a gene of interest in a host cell. Unless otherwise specified, the term "vector" may mean one allowing the nucleic acid sequence contained therein to be expressed after insertion into the host cell genome and/or one allowing the nucleic acid sequence to be expressed independently. This vector comprises essential regulatory elements operably linked so that an inserted gene can be expressed. As used herein, the term "operably linked" means that a gene of interest and regulatory sequences thereof are functionally linked together in a manner enabling gene expression, and the "regulatory elements" include a promoter for initiating transcription, any operator sequence for regulating transcription, a sequence encoding suitable mRNA ribosome-binding sites, and a sequence for regulating termination of transcription and translation.

The vector in the present invention is not particularly limited as long as it may replicate in a host cell, and any vector known in the art may be used. Examples of the vector include a natural or recombinant plasmid, cosmid, virus and bacteriophage. Examples of a phage vector or cosmid vector include, but are not limited to, pWE15, M13, λMBL3, λMBL4, λIXII, λASHII, λAPII, λt10, λt11, Charon4A, and Charon21A, and examples of a plasmid vector include, but are not limited to, pBR series, pUC series, pBluescriptII series, pGEM series, pTZ series, pCL series, and pET series.

The vector may typically be constructed as a vector for cloning or as a vector for expression. The vector for expression may be a conventional vector that is used in the art to express a foreign gene or protein in a plant, animal, or microorganism, and may be constructed through various methods known in the art.

As used in the present invention, the term "recombinant vector" may be transformed into a suitable host cell, and then may replicate regardless of the genome of the host cell or may be integrated into the genome itself. In this case, the "suitable host cell" may contain a replication origin, which is a particular nucleotide sequence which enables the vector to replicate in the suitable host cell and from which replication starts. For example, when the vector used is an expression vector and uses a prokaryotic cell as a host, the vector generally comprises a strong promoter capable of promoting transcription (e.g., pLλ promoter, CMV promoter, trp promoter, lac promoter, tac promoter, T7 promoter, etc.), a ribosome binding site for initiation of translation, and a transcription/translation termination sequence. When a eukaryotic cell is used as a host, the vector comprises a replication origin operating in the eukaryotic cell, and examples of the replication origin include, but are not limited to, an f1 replication origin, an SV40 replication origin, a pMB1 replication origin, an adeno replication origin, an AAV replication origin, and a BBV replication origin. In addition, the recombinant vector may comprise a promoter derived from the genome of a mammalian cell (e.g., metallothionein promoter) or a promoter derived from a mammalian virus (e.g., adenovirus late promoter, vaccinia virus 7.5K promoter, SV40 promoter, cytomegalovirus promoter, HSV-tk promoter, etc.), and generally has a polyadenylation sequence as a transcription termination sequence.

The recombinant vector may comprise a selection marker. The selection marker serves to select a transformant (host cell) transformed with the vector, and since only cells expressing the selection marker can survive in the medium treated with the selection marker, it is possible to select transformed cells. Representative examples of the selection marker include, but are not limited to, kanamycin, streptomycin, and chloramphenicol.

The transformant may be produced by inserting the recombinant vector into a host cell, and the transformant may be obtained by introducing the recombinant vector into an appropriate host cell. The host cell is a cell capable of stably and continuously cloning or expressing the expression vector, and any host cell known in the art may be used.

Where the vector is transformed into prokaryotic cells to generate recombinant microorganisms, examples of host cells that may be used include, but are not limited to, *E. coli* sp. strains such as *E. coli* DH5α, *E. coli* JM109, *E. coli* BL21, *E. coli* RR1, *E. coli* LE392, *E. coli* B, *E. coli* X 1776, *E. coli* W3110, and *E. coli* XL1-Blue, *Bacillus* sp. strains such as *Bacillus subtilis* and *Bacillus thuringiensis*, *Coryne-*

*bacterium* sp. strains such as *Corynebacterium glutamicum* and *Corynebacterium stationis*, and various Enterobacteriaceae strains such as *Salmonella typhimurium, Serratia marcescens*, and *Pseudomonas* species.

Where the vector is transformed into eukaryotic cells to generate recombinant microorganisms, examples of host cells that may be used include, but are not limited to, yeast (e.g., *Saccharomyces cerevisiae*), insect cells, plant cells and animal cells, such as Sp2/0, CHO K1, CHO DG44, PER.C6, W138, BHK, COS7, 293, HepG2, Huh7, 3T3, RIN, and MDCK cell lines.

As used in the present invention, the term "transformation" refers to a phenomenon in which external DNA is introduced into a host cell, thereby artificially causing genetic changes, and the term "transformant" refers to a host cell into which external DNA has been introduced and in which the expression of the gene of interest is stably maintained.

The transformation may be performed using a suitable vector introduction technique selected depending on the host cell, so that the gene of interest or a recombinant vector comprising the same may be expressed in the host cell. For example, introduction of the vector may be performed by electroporation, heat-shock, calcium phosphate ($CaPO_4$) precipitation, calcium chloride ($CaCl_2$) precipitation, microinjection, polyethylene glycol (PEG) method, DEAE-dextran method, cationic liposome method, lithium acetate-DMSO method, or any combination thereof, without being limited thereto. As long as the transformed gene may be expressed in the host cell, it may be inserted into the chromosome of the host cell, or may exist extrachromosomally, without being limited thereto.

The transformant may include a cell transfected, transformed, or infected with the recombinant vector of the present invention in vivo or in vitro, and may be used in the same sense as a recombinant host cell, a recombinant cell, or a recombinant microorganism.

Genes inserted into the recombinant vector of the present invention may be introduced into a host cell such as a *Corynebacterium* sp. strain by homologous recombination crossover.

According to one embodiment of the present invention, the transformant may be a *Corynebacterium* sp. microorganism.

The *Corynebacterium* sp. microorganism may be, but is not limited to, *Corynebacterium glutamicum, Corynebacterium crudilactis, Corynebacterium deserti, Corynebacterium callunae, Corynebacterium suranareeae, Corynebacterium lubricantis, Corynebacterium doosanense, Corynebacterium efficiens, Corynebacterium uterequi, Corynebacterium stationis, Corynebacterium pacaense, Corynebacterium singulare, Corynebacterium humireducens, Corynebacterium marinum, Corynebacterium halotolerans, Corynebacterium spheniscorum, Corynebacterium freiburgense, Corynebacterium striatum, Corynebacterium canis, Corynebacterium ammoniagenes, Corynebacterium renale, Corynebacterium pollutisoli, Corynebacterium imitans, Corynebacterium caspium, Corynebacterium testudinoris, Corynebacaterium pseudopelargi*, or *Corynebacterium flavescens*.

The transformant in the present invention may be a strain either comprising the above-described 5-dehydro-2-deoxygluconokinase variant or a polynucleotide encoding the same or comprising the vector comprising the same, a strain expressing the 5-dehydro-2-deoxygluconokinase variant or the polynucleotide, or a strain having activity for the 5-dehydro-2-deoxygluconokinase variant, without being limited thereto.

The transformant of the present invention may comprise other protein variants or genetic mutations, in addition to the 5-dehydro-2-deoxygluconokinase variant.

According to one embodiment of the present invention, the transformant may have the ability to produce inosinic acid.

The 5'-inosinic acid is a nucleic acid-based compound that gives flavor to food, especially umami (savory) taste, and is used with the same meaning as inosine monophosphate (IMP).

The transformant may naturally have the ability to produce 5'-inosinic acid or may be one artificially endowed with the ability to produce 5'-inosinic acid.

According to one embodiment of the present invention, the transformant may have an increased ability to produce 5'-inosinic acid, due to a change in 5-dehydro-2-deoxygluconokinase activity.

As used in the present invention, the term "increased ability to produce" means that 5'-inosinic acid productivity has increased compared to that of the parent strain. As used herein, the term "parent strain" refers to a wild-type strain or mutant strain to be mutated, and includes a strain that is to be mutated directly or to be transformed with a recombinant vector or the like. In the present invention, the parent strain may be a wild-type *Corynebacterium* sp. strain or a *Corynebacterium* sp. strain mutated from the wild-type strain.

The transformant according to the present invention exhibits an increased ability to produce 5'-inosinic acid compared to the parent strain, due to the change in 5-dehydro-2-deoxygluconokinase activity caused by introduction of the 5-dehydro-2-deoxygluconokinase variant thereinto. More specifically, the amount of 5'-inosinic acid produced by the transformant may be at least 1%, 5%, 10%, 15%, 20%, 25%, 30%, 35%, 40%, 45%, 50%, 55%, 60%, 65%, 70%, 75%, 80%, 85%, 90%, 95%, or 100% higher than that produced by the parent strain, or may be 1.1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold higher than that produced by the parent strain, without being limited thereto. For example, the amount of 5'-inosinic acid produced by the transformant comprising the 5-dehydro-2-deoxygluconokinase variant may be at least 5%, specifically 5 to 50% (preferably 10 to 40%) higher than that produced by the parent strain.

Still yet another aspect of the present invention provides a method for producing 5'-inosinic acid, comprising steps of: culturing the transformant in a medium; and recovering 5'-inosinic acid from the transformant or the medium in which the transformant has been cultured.

The culturing may be performed using a suitable medium and culture conditions known in the art, and any person skilled in the art may easily adjust and use the medium and the culture conditions. Specifically, the medium may be a liquid medium, without being limited thereto. Examples of the culturing method include, but are not limited to, batch culture, continuous culture, fed-batch culture, or a combination thereof.

According to one embodiment of the present invention, the medium should meet the requirements of a specific strain in a proper manner, and may be appropriately modified by a person skilled in the art. For culture media for *Escherichia* sp. strains, reference may be made to, but not limited to, a known document (Manual of Methods for General Bacteriology, American Society for Bacteriology, Washington D.C., USA, 1981).

According to one embodiment of the present invention, the medium may contain various carbon sources, nitrogen sources, and trace element components. Examples of carbon sources that may be used include: sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These substances may be used individually or as a mixture, without being limited thereto. Examples of nitrogen sources that may be used include peptone, yeast extract, meat extract, malt extract, corn steep liquor, soybean meal, urea, or inorganic compounds such as ammonium sulfate, ammonium chloride, ammonium phosphate, ammonium carbonate, and ammonium nitrate. The nitrogen sources may also be used individually or as a mixture, without being limited thereto. Examples of phosphorus sources that may be used include, but are not limited to, potassium dihydrogen phosphate or dipotassium hydrogen phosphate or the corresponding sodium-containing salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be used in the culture medium. The medium or individual components may be added to the culture medium batchwise or in a continuous manner by a suitable method during culturing, without being limited thereto.

According to one embodiment of the present invention, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20° C. to 45° C., for example, 25° C. to 40° C. The culturing may be continued until a desired amount of a useful substance is produced. For example, the culturing time may be 10 hours to 160 hours.

According to one embodiment of the present invention, in the step of recovering 5'-inosinic acid from the cultured transformant or the medium in which the transformant has been cultured, the produced 5'-inosinic acid may be collected or recovered from the medium using a suitable method known in the art depending on the culture method. Examples of a method that may be used to recover the produced 5'-inosinic acid include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion), and the like.

According to one embodiment of the present invention, the step of recovering 5'-inosinic acid may be performed by centrifuging the culture medium at a low speed to remove biomass and separating the obtained supernatant through ion-exchange chromatography.

According to one embodiment of the present invention, the step of recovering 5'-inosinic acid may include a process of purifying the 5'-inosinic acid.

Advantageous Effects

The 5-dehydro-2-deoxygluconokinase variant according to the present invention is obtained by substituting one or more amino acids in the amino acid sequence constituting 5-dehydro-2-deoxygluconokinase to change the activity of the protein, and a recombinant microorganism comprising the 5-dehydro-2-deoxygluconokinase variant is capable of efficiently producing 5'-inosinic acid.

BRIEF DESCRIPTION OF DRAWINGS

FIG. 1 shows the structure of a pK19msb plasmid according to one embodiment of the present invention.

MODE FOR INVENTION

Hereinafter, the present invention will be described in more detail. However, this description is merely presented by way of example to facilitate the understanding of the present invention, and the scope of the present invention is not limited by this exemplary description.

Example 1. Construction of Strain Expressing 5-Dehydro-2-Deoxygluconokinase Variant To evaluate the effect of a variant (SEQ ID NO: 2) having a substitution of asparagine (N) for serine (S) at position 146 in the amino acid sequence of 5-dehydro-2-deoxygluconokinase (SEQ ID NO: 4) on the production of 5'-inosinic acid, the present inventors constructed a vector for expressing the 5-dehydro-2-deoxygluconokinase variant and a strain into which the vector has been introduced.

1-1. Construction of Vector for Expression of 5-Dehydro-2-Deoxygluconokinase Variant Using the genomic DNA of wild-type *Corynebacterium stationis* ATCC6872 as a template, PCR reactions were performed using a primer pair of primers 1 and 2 and a primer pair of primers 3 and 4, respectively. Thereafter, using the two PCR products as templates, overlapping PCR was performed using a primer pair of primers 1 and 4 to obtain a single fragment. The PCR fragment and a pK19msb plasmid (SEQ ID NO: 5) were treated with the restriction enzyme smaI (NEB) and ligated together using T4 ligase. The resulting plasmid was named pK_DD.

The PCR amplification was performed using Pfu PreMix (Bioneer) under the following conditions: denaturation at 95° C. for 5 min, and then 30 cycles, each consisting of 95° C. for 30 sec, 58° C. for 30 sec, and 72° C. for 1 min and 30 sec, followed by reaction at 72° C. for 5 min.

The primer sequences used for plasmid construction are shown in Table 1 below.

TABLE 1

| Primer name | SEQ ID NO. | Primer sequence (5'→3') |
| --- | --- | --- |
| Primer 1 | 6 | AATGTGCTATTGTCAGGACATGC |
| Primer 2 | 7 | GGCTCTTCGTTTAAACCGGTCA |

TABLE 1-continued

| Primer name | SEQ ID NO. | Primer sequence (5'→3') |
|---|---|---|
| Primer 3 | 8 | TGACCGGTTTAAACGAAGAGCC |
| Primer 4 | 9 | ACCTTCTGACTTAGGGCTGCTT |

1-2. Construction of Mutant Strain into Which 5-Dehydro-2-Deoxygluconokinase Variant Has Been Introduced An electrocompetent cell preparation method, a modification of the method of van der Rest et al., was used as a method for transformation of *Corynebacterium stationis* KCCM13339P.

First, *Corynebacterium stationis* KCCM13339P was primarily cultured in 10 mL of 2YT medium (containing 16 g/l of tryptone, 10 g/l of yeast extract, and 5 g/l of sodium chloride) supplemented with 2% glucose, thus preparing a seed culture. Isonicotinic acid hydrazine at a concentration of 1 mg/ml and 2.5% glycine were added to 100 ml of 2YT medium free of glucose. Next, the seed culture was inoculated into the 2YT medium to reach an $OD_{610}$ value of 0.3, and then cultured at 30° C. and 180 rpm for 5 to 8 hours so that the $OD_{610}$ value reached 0.6 to 0.7. The culture was kept on ice for 30 minutes, and then centrifuged at 3,500 rpm at 4° C. for 10 minutes. Thereafter, the supernatant was discarded and the precipitated *Corynebacterium stationis* KCCM13339P was washed 4 times with a 10% glycerol solution and finally re-suspended in 0.5 ml of a 10% glycerol solution, thereby preparing competent cells. Electroporation was performed using a Bio-Rad electroporator. The prepared competent cells and the constructed pK_DD vector were placed in an electroporation cuvette (0.2 mm), and then subjected to electroporation under conditions of 2.5 kV, 200Ω and 12.5 pF. Immediately after completion of the electroporation, 1 ml of a regeneration (RG) medium (containing 18.5 g/l brain heart infusion and 0.5 M sorbitol) was added to the cells which were then heat-treated at 46° C. for 6 minutes. Next, the cells were cooled at room temperature, transferred into a 15-ml cap tube, incubated at 30° C. for 2 hours, and plated on a selection medium (containing 5 g/l tryptone, 5 g/l NaCl, 2.5 g/l yeast extract, 18.5 g/l brain heart infusion powder, 15 g/l agar, 91 g/l sorbitol, and 20 pg/l kanamycin). The cells were cultured at 30° C. for 72 hours, and the generated colonies were cultured in medium until the stationary phase to induce secondary recombination. Then, the cells were diluted to $10^{-5}$ to $10^{-7}$, and plated on an antibiotic-free plate medium (containing 10% sucrose), and a strain having no kanamycin resistance and grown on the medium containing 10% sucrose was selected and named IDD-1.

Experimental Example 1. Evaluation of 5'-Inosinic Acid Productivity of Strain Expressing 5-Dehydro-2-Deoxygluconokinase Variant 5'-Inosinic acid productivity was compared between the parent strain KCCM13339P and the mutant strain IDD-1 into which the 5-dehydro-2-deoxygluconokinase variant has been introduced.

Each strain (parent strain or mutant strain) was inoculated at 1% by volume into a 100-mL flask containing 10 mL of the medium for 5'-inosinic acid production shown in Table 2 below, and cultured with shaking at 200 rpm at 34° C. for 45 hours. After completion of the culturing, the concentration of 5'-inosinic acid in the medium was measured using HPLC (Agilent), and the results are shown in Table 3 below.

TABLE 2

| Component | Content |
|---|---|
| Glucose | 70 g/L |
| $(NH_4)_2SO_4$ | 2 g/L |
| $MgSO_4$ | 1 g/L |
| Urea | 2 g/L |
| Yeast extract | 20 g/L |
| $KH_2PO_4$ | 2 g/L |
| $FeSO_4$ | 10 mg/L |
| $MnSO_4$ | 10 mg/L |
| Thiamine_HCl | 5 mg/L |
| biotin | 20 ug/L |
| Cystein | 20 mg/L |
| Bata-alanine | 20 mg/L |
| Adenine | 30 mg/L |

TABLE 3

| Strain | 5'-inosinic acid production (g/L) |
|---|---|
| KCCM13339P | 19.8 |
| IDD-1 | 23.0 |

As shown in Table 3 above, it was confirmed that the amount of 5'-inosinic acid produced by the mutant strain into which the 5-dehydro-2-deoxygluconokinase variant has been introduced was increased by about 16% compared to that produced by the parent strain, due to substitution of serine at position 146 with asparagine. These results suggest that introduction of a point mutation into 5-dehydro-2-deoxygluconokinase provides a significant effect on 5'-inosinic acid productivity.

So far, the present invention has been described with reference to the preferred embodiments. Those of ordinary skill in the art to which the present invention pertains will appreciate that the present invention may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description, and all differences within the scope equivalent thereto should be construed as being included in the present invention Accession Number Depository Authority: Korean Culture Center of Microorganisms (KCCM)
Accession Number: KCCM13339P
Deposit Date: Mar. 29, 2023

The invention claimed is:

1. A 5-dehydro-2-deoxygluconokinase variant consisting of the amino acid sequence of SEQ ID NO: 2 in which serine at position 146 in the amino acid sequence of SEQ ID NO: 4 is substituted with asparagine.

2. A polynucleotide encoding the variant of claim 1.

3. A transformant comprising the variant of claim 1.

4. The transformant of claim 3, which is a *Corynebacterium* sp. microorganism.

5. The transformant of claim 3, which has ability to produce 5'-inosinic acid.

6. A method for producing 5'-inosinic acid, comprising steps of:
   culturing the transformant of claim 3 in a medium; and
   recovering 5'-inosinic acid from the transformant or the medium in which the transformant has been cultured.

7. A transformant comprising the polynucleotide of claim 2.

* * * * *

SEQUENCE LISTING

Sequence total quantity: 9
SEQ ID NO: 1             moltype = DNA   length = 957

```
FEATURE                 Location/Qualifiers
source                  1..957
                        mol_type = other DNA
                        organism = synthetic construct
SEQUENCE: 1
atggcgtatt taactagcgc tcacgaagtt ctggccatcg gcaggcttgg cgtggatatc    60
tatccactac agtccggcgt tgggctagaa gaggtatctt ctttcggcaa atacctaggc   120
ggatccgcag caaatgtctc tgttgcagcc gcacggcacg gcacaattc cgcactgcta    180
tcacgagtag gcaatgaccc actgggtaag tacctgctca atgagctgga aaggctcggg   240
gtagataatc agtacgtcgc tactgatccg acttataaaa ccccgctgac tttgtgcgaa   300
attttcccac cagatgattt cccgctgtac ttctaccgcg agcccaaagc tccggatatg   360
tgcatcgagt cctctgacgt caacctcgaa gatgtccgcg atgcagaaat cttgtggttt   420
accctgaccg gtttaaacga gagccaagcc cgcggcgcac atcaggaaat cctgaacacc   480
cgcgcccggc gcaagcacac catcttggac ttggactacc gcgacatgtt ctggaattcc   540
aagcaggaag caacagagca ggcacagtgg gcactcgagc atgccaccgt tgcggtcggt   600
aacaaggaag aatgcgaggt cgccatcggc gaaaccgaac agaacgcgc cggcaaggcg    660
ttgttggaac atggcgtgaa gttggccatc gttaagcaag gccccaaagg cgtgctggcc   720
atgactgaag atgaaaccgt cgaagtgcca ccggtgtggg tcgatgttgt caacggcctc   780
ggcgctggcg atgccttcgg tggcgcgctg tgccacggtc tgttgtccga ctggccactc   840
gaaaaagtcc tgcgctttgc caacgcggca ggctcggtgg ttgccggacg cttagagtgc   900
agcaccgcca tgccaaccac tgaagaagtt gaagcagccc taagtcagaa ggtctag     957

SEQ ID NO: 2           moltype = AA    length = 318
FEATURE                Location/Qualifiers
source                 1..318
                       mol_type = protein
                       organism = synthetic construct
SEQUENCE: 2
MAYLTSAHEV LAIGRLGVDI YPLQSGVGLE EVSSFGKYLG GSAANVSVAA ARHGHNSALL    60
SRVGNDPLGK YLLNELERLG VDNQYVATDP TYKTPLTLCE IFPPDDFPLY FYREPKAPDM   120
CIESSDVNLE DVRDAEILWF TLTGLNEEPS RGAHQEILNT RARRKHTILD LDYRDMFWNS   180
KQEATEQAQW ALEHATVAVG NKEECEVAIG ETEPERAGKA LLEHGVKLAI VKQGPKGVLA   240
MTEDETVEVP PVWVDVVNGL GAGDAFGGAL CHGLLSDWPL EKVLRFANAA GSVVAGRLEC   300
STAMPTTEEV EAALSQKV                                                318

SEQ ID NO: 3           moltype = DNA    length = 957
FEATURE                Location/Qualifiers
source                 1..957
                       mol_type = genomic DNA
                       organism = Corynebacterium stationis
SEQUENCE: 3
atggcgtatt taactagcgc tcacgaagtt ctggccatcg gcaggcttgg cgtggatatc    60
tatccactac agtccggcgt tgggctagaa gaggtatctt ctttcggcaa atacctaggc   120
ggatccgcag caaatgtctc tgttgcagcc gcacggcacg gcacaattc cgcactgcta    180
tcacgagtag gcaatgaccc actgggtaag tacctgctca atgagctgga aaggctcggg   240
gtagataatc agtacgtcgc tactgatccg acttataaaa ccccgctgac tttgtgcgaa   300
attttcccac cagatgattt cccgctgtac ttctaccgcg agcccaaagc tccggatatg   360
tgcatcgagt cctctgacgt caacctcgaa gatgtccgcg atgcagaaat cttgtggttt   420
accctgaccg gtttaagcga gagccaagcc cgcggcgcac atcaggaaat cctgaacacc   480
cgcgcccggc gcaagcacac catcttggac ttggactacc gcgacatgtt ctggaattcc   540
aagcaggaag caacagagca ggcacagtgg gcactcgagc atgccaccgt tgcggtcggt   600
aacaaggaag aatgcgaggt cgccatcggc gaaaccgaac agaacgcgc cggcaaggcg    660
ttgttggaac atggcgtgaa gttggccatc gttaagcaag gccccaaagg cgtgctggcc   720
atgactgaag atgaaaccgt cgaagtgcca ccggtgtggg tcgatgttgt caacggcctc   780
ggcgctggcg atgccttcgg tggcgcgctg tgccacggtc tgttgtccga ctggccactc   840
gaaaaagtcc tgcgctttgc caacgcggca ggctcggtgg ttgccggacg cttagagtgc   900
agcaccgcca tgccaaccac tgaagaagtt gaagcagccc taagtcagaa ggtctag     957

SEQ ID NO: 4           moltype = AA    length = 318
FEATURE                Location/Qualifiers
source                 1..318
                       mol_type = protein
                       organism = Corynebacterium stationis
SEQUENCE: 4
MAYLTSAHEV LAIGRLGVDI YPLQSGVGLE EVSSFGKYLG GSAANVSVAA ARHGHNSALL    60
SRVGNDPLGK YLLNELERLG VDNQYVATDP TYKTPLTLCE IFPPDDFPLY FYREPKAPDM   120
CIESSDVNLE DVRDAEILWF TLTGLSEEPS RGAHQEILNT RARRKHTILD LDYRDMFWNS   180
KQEATEQAQW ALEHATVAVG NKEECEVAIG ETEPERAGKA LLEHGVKLAI VKQGPKGVLA   240
MTEDETVEVP PVWVDVVNGL GAGDAFGGAL CHGLLSDWPL EKVLRFANAA GSVVAGRLEC   300
STAMPTTEEV EAALSQKV                                                318

SEQ ID NO: 5           moltype = DNA    length = 5719
FEATURE                Location/Qualifiers
source                 1..5719
                       mol_type = other DNA
                       organism = synthetic construct
SEQUENCE: 5
tgccgcaagc actcagggcg caagggctgc taaaggaagc ggaacacgta gaaagccagt    60
ccgcagaaac ggtgctgacc ccggatgaat gtcagctact gggctatctg acaagggaa    120
```

```
aacgcaagcg caaagagaaa gcaggtagct tgcagtgggc ttacatggcg atagctagac    180
tgggcggttt tatggacagc aagcgaaccg gaattgccag ctggggcgcc ctctggtaag    240
gttgggaagc cctgcaaagt aaactggatg gctttcttgc cgccaaggat ctgatggcgc    300
aggggatcaa gatctgatca agagacagga tgaggatcgt ttcgcatgat tgaacaagat    360
ggattgcacg caggttctcc ggccgcttgg gtggagaggc tattcggcta tgactgggca    420
caacagacaa tcggctgctc tgatgccgcc gtgttccggc tgtcagcgca ggggcgcccg    480
gttcttttg tcaagaccga cctgtccggt gccctgaatg aactccaaga cgaggcagcg    540
cggctatcgt ggctggccac gacgggcgtt ccttgcgcag ctgtgctcga cgttgtcact    600
gaagcgggaa gggactggct gctattgggc gaagtgccgg ggcaggatct cctgtcatct    660
caccttgctc ctgccgagaa agtatccatc atggctgatg caatgcggcg gctgcatacg    720
cttgatccgg ctacctgccc attcgaccac caagcgaaac atcgcatcga gcgagcacgt    780
actcggatgg aagccggtct tgtcgatcag gatgatctgg acgaagagca tcagggctc    840
gcgccagccg aactgttcgc caggctcaag gcgcggatgc ccgacggcga ggatctcgtc    900
gtgacccatg gcgatgcctg cttgccgaat atcatggtgg aaaatggccg cttttctgga    960
ttcatcgact gtggccggct gggtgtggcg gaccgctatc aggacatagc gttggctacc   1020
cgtgatattg ctgaagagct tggcggcgaa tgggctgacc gcttcctcgt gctttacggt   1080
atcgccgctc ccgattcgca gcgcatcgcc ttctatcgcc ttcttgacga gttcttctga   1140
gcgggactct ggggttcgct agaggatcga tcctttttaa cccatcacat atacctgccg   1200
ttcactatta tttagtgaaa tgagatatta tgatattttc tgaattgtga ttaaaaaggc   1260
aactttatgc ccatgcaaca gaaactataa aaaatacaga gaatgaaaag aaacagatag   1320
atttttagt tctttaggcc cgtagtctgc aaatccttt atgattttct atcaaacaaa   1380
agaggaaaat agaccagttg caatccaaac gagagtctaa tagaatgagg tcgaaaagta   1440
aatcgcgcgg gtttgttact gataaagcag gcaagaccta aaatgtgtaa agggcaaagt   1500
gtatactttg gcgtcacccc ttacatattt taggtctttt tttattgtgc gtaactaact   1560
tgccatcttc aaacaggagg gctggaagaa gcagaccgct aacacagtac ataaaaaggg   1620
agacatgaac gatgaacatc aaaaagtttg caaaacaagc aacagtatta acctttacta   1680
ccgcactgct ggcaggaggc gcaactcaag cgtttgcgaa agaaacgaac caaaagccat   1740
ataaggaaac atacggcatt tcccatatta cacgccatga tatgctgcaa atccctgaac   1800
agcaaaaaaa tgaaaatat caagtttctg aatttgattc gtccacaatt aaaaatatct   1860
cttctgcaaa aggcctggac gtttgggaca gctggccatt acaaaacgct gacggcactg   1920
tcgcaaacta tcacggctac cacatcgtct ttgcattagc cggagatcct aaaaatgcgg   1980
atgacacatc gatttacatg ttctatcaaa aagtcggcga aacttctatt gacagctgga   2040
aaaacgctgg ccgcgtcttt aaagacagcg acaaattcga tgcaaatgat tctatcctaa   2100
aagaccaaac acaagaatgg tcaggttcag ccacatttac atctgacgga aaaatccgtt   2160
tattctacac tgatttctcc ggtaaacatt acggcaaaca aacactgaca actgcacaag   2220
ttaacgtatc agcatcagac agctctttga acatcaacgg tgtagaggat tataaatcaa   2280
tctttgacgg tgacgaaaa acgtatcaaa atgtacagca gttcatcgat gaaggcaact   2340
acagctcagg cgacaaccat acgctgagag atcctcacta cgtagaagat aaaggccaca   2400
aatactagt atttgaagca aacactggaa ctgaagatgg ctaccaaggc gaagaatctt   2460
tatttaacaa agcatactat ggcaaaagca catcattctt ccgtcaagaa agtcaaaaac   2520
ttctgcaaag cgataaaaaa cgcacggctg agttagcaaa cggcgctctc ggtatgattg   2580
agctaaacga tgattacaca ctgaaaaaag tgatgaaacc gctgattgca tctaacacag   2640
taacgatga aattgaacgc gcgaacgtct ttaaaatgaa cggcaaatgg tacctgttca   2700
ctgactcccg cggatcaaaa atgacgattg acggcattac gtctaacgat atttacatgc   2760
ttggttatgt ttctaattct ttaactggcc catacaagcc gctgaacaaa actgccttg   2820
tgttaaaaat ggatcttgat cctaacgatg taaccttac ttactcacac ttcgctgtac   2880
ctcaagcgaa aggaaacaat gtcgtgatta caagctatat gacaaacgga ggattctacg   2940
cagacaaaca atcaacgttt gcgccgagct tcctgctgaa catcaaaggc aagaaaacat   3000
ctgttgtcaa agacagcatc cttgaacaag acaattaac agttaacaaa taaaacgca   3060
aaagaaatg ccgatgggta ccgagcgaaa tgaccgacca agcgacgccc aacctgccat   3120
cacgagattt cgattccacc gccgccttct atgaaaggt gggcttcgga atcgttttcc   3180
gggacgccct cgcggacgtg ctcatagtcc acgacgcccg tgattttgta gccctggccg   3240
acggccagca ggtaggccga caggctcatg ccggccgccg ccgccttttc ctcaatcgct   3300
cttcgttcgt ctggaaggca gtacaccttg ataggtgggc tgcccttcct ggttggcttg   3360
gtttcatcag ccatccgctt gccctcatct gttacgccgg cggtagccgg ccagcctgg   3420
agagcaggat tccgttgag caccgccagg tgcgaataag ggacagtgaa gaaggaacac   3480
ccgctcgcgg gtgggcctac ttcacctatc ctgcccgct gacgccgttg gatacaccaa   3540
ggaaagtcta cacgaaccct ttggcaaaat cctgtatatc gtgcgaaaaa ggatggatat   3600
accgaaaaaa tcgctataat gaccccgaag cagggttatg cagcggaaaa gcgctgcttc   3660
cctgctgttt tgtggaatat ctaccgactg gaaacaggga aatgcaggaa attactgaac   3720
tgagggaca ggcgagagac gatgccaaag agctcctgaa aatctcgata actcaaaaa   3780
tacgcccggt agtgatctta tttcattatg gtgaaagttg gaacctctta cgtgccgatc   3840
aacgtctcat tttcgccaaa agttggccca gggcttcccg gtatcaacag ggacaccagg   3900
atttatttat tctgcgaagt gatcttccgt cacaggtatt tattcggcgc aaagtgcgtc   3960
gggtgatgct gccaacttac tgatttagtg tatgatggtg tttttgaggt gctccagtgg   4020
cttctgtttc tatcagctcc tgaaaatctc gataactcaa aaaatacgcc cggtagtgat   4080
cttatttcat tatggtgaaa gttggaacct cttacgtgcc gatcaacgtc tcattttcgc   4140
caaaagttgg cccagggctt cccggtatca acagggacac caggatttat ttattctgcg   4200
aagtgatctt ccgtcacagg tatttattcg gcgcaaagtg cgtcgggtga tgctgccaac   4260
ttactgattt agtgtatgat ggtgttttg aggtgctcca gtggcttctg tttctatcag   4320
gctggatga tcctccagcg cggggatctc atgctggagt tcttcgccca ccccaaaagg   4380
atctaggtga agatcctttt tgataatctc atgaccaaaa tcccttaacg tgagttttcg   4440
ttccactgag cgtcagaccc cgtagaaaag atcaaaggat cttcttgaga tcctttttt   4500
ctgcgcgtaa tctgctgctt gcaaacaaaa aaaccaccgc taccaggcgg tgtttgtttg   4560
ccggatcaag agctaccaac tctttttccg aaggtaactg gcttcagcag agcgcagata   4620
ccaaatactg ttcttctagt gtagccgtag ttaggccacc acttcaagaa ctctgtagca   4680
ccgcctacat acctcgctct gctaatcctg ttaccagtgg ctgctgccag tggcgataag   4740
tcgtgtctta ccgggttgga ctcaagacga tagttaccgg ataaggcgca gcggtcgggc   4800
tgaacggggg gttcgtgcac acagcccagc ttggagcgaa cgacctacac cgaactgaga   4860
```

```
tacctacagc gtgagctatg agaaagcgcc acgcttcccg aagggagaaa ggcggacagg    4920
tatccggtaa gcggcagggt cggaacagga gagcgcacga gggagcttcc aggggggaaac   4980
gcctggtatc tttatagtcc tgtcgggttt cgccacctct gacttgagcg tcgattttg    5040
tgatgctcgt caggggggcg gagcctatgg aaaaacgcca gcaacgcggc cttttacgg    5100
ttcctggcct tttgctggcc ttttgctcac atgttctttc ctgcgttatc ccctgattct   5160
gtggataacc gtattaccgc ctttgagtga gctgataccg ctcgccgcag ccgaacgacc   5220
gagcgcagcg agtcagtgag cgaggaagcg gaagagcgcc caatacgcaa accgcctctc   5280
cccgcgcgtt ggccgattca ttaatgcagc tggcacgaca ggtttcccga ctggaaagcg   5340
ggcagtgagc gcaacgcaat taatgtgagt tagctcactc attaggcacc ccaggcttta   5400
cactttatgc ttccggctcg tatgttgtgt ggaattgtga gcggataaca atttcacaca   5460
ggaaacagct atgacatgat tacgccaagc ttgcatgcct gcaggtcgac tctagaggat   5520
ccccgggtac cgagctcgaa ttcactggcc gtcgttttac aacgtcgtga ctgggaaaac   5580
cctggcgtta cccaacttaa tcgccttgca gcacatcccc ctttcgccag ctggcgtaat   5640
agcgaagagg cccgcaccga tcgcccttcc caacagttgc gcagcctgaa tggcgaatgg   5700
cgataagcta gcttcacgc                                                 5719

SEQ ID NO: 6          moltype = DNA  length = 23
FEATURE               Location/Qualifiers
source                1..23
                      mol_type = other DNA
                      organism = synthetic construct
SEQUENCE: 6
aatgtgctat tgtcaggaca tgc                                           23

SEQ ID NO: 7          moltype = DNA  length = 22
FEATURE               Location/Qualifiers
source                1..22
                      mol_type = other DNA
                      organism = synthetic construct
SEQUENCE: 7
ggctcttcgt ttaaaccggt ca                                            22

SEQ ID NO: 8          moltype = DNA  length = 22
FEATURE               Location/Qualifiers
source                1..22
                      mol_type = other DNA
                      organism = synthetic construct
SEQUENCE: 8
tgaccggttt aaacgaagag cc                                            22

SEQ ID NO: 9          moltype = DNA  length = 22
FEATURE               Location/Qualifiers
source                1..22
                      mol_type = other DNA
                      organism = synthetic construct
SEQUENCE: 9
accttctgac ttagggctgc tt                                            22
```